(12) United States Patent
Wu

(10) Patent No.: US 9,182,393 B2
(45) Date of Patent: Nov. 10, 2015

(54) MICRODEPOSITION SYSTEM FOR A BIOSENSOR

(75) Inventor: Huan-Ping Wu, Granger, IN (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 1174 days.

(21) Appl. No.: 12/132,954

(22) Filed: Jun. 4, 2008

(65) Prior Publication Data
US 2009/0305906 A1    Dec. 10, 2009

Related U.S. Application Data

(60) Provisional application No. 60/942,437, filed on Jun. 6, 2007.

(51) Int. Cl.
| | |
|---|---|
| *B01L 3/00* | (2006.01) |
| *B01L 9/00* | (2006.01) |
| *B05C 1/00* | (2006.01) |
| *B05D 5/00* | (2006.01) |
| *G01N 33/543* | (2006.01) |
| *B01J 19/00* | (2006.01) |
| *C40B 60/14* | (2006.01) |
| *C40B 40/00* | (2006.01) |

(Continued)

(52) U.S. Cl.
CPC ....... *G01N 33/54373* (2013.01); *B01J 19/0046* (2013.01); *B01L 3/0248* (2013.01); *C40B 60/14* (2013.01); *B01J 2219/00387* (2013.01); *B01J 2219/00509* (2013.01); *B01J 2219/00603* (2013.01); *B01J 2219/00605* (2013.01); *B01J 2219/00653* (2013.01); *B01J 2219/00659* (2013.01); *B01J 2219/00725* (2013.01); *B01L 3/0275* (2013.01); *B01L 9/00* (2013.01); *B01L 2300/0819* (2013.01); *B01L 2400/025* (2013.01); *G01N 2035/1037* (2013.01)

(58) Field of Classification Search
None
See application file for complete search history.

(56) References Cited

U.S. PATENT DOCUMENTS

| 6,101,946 A | 8/2000 | Martinsky | |
|---|---|---|---|
| 6,475,440 B1 * | 11/2002 | Bochkariov | 422/519 |

(Continued)

FOREIGN PATENT DOCUMENTS

| WO | WO 9904896 | 2/1999 |
|---|---|---|
| WO | WO 9934214 | 7/1999 |

(Continued)

OTHER PUBLICATIONS

EPO, "Search Report and Written Opinion for PCT/US2008/065658", Jan. 5, 2009, Publisher: International Searching Authority.

(Continued)

*Primary Examiner* — Lyle Alexander
*Assistant Examiner* — Jennifer Wecker
(74) *Attorney, Agent, or Firm* — Nixon Peabody LLP

(57) ABSTRACT

A microdeposition pin having a contact surface with at least one concave edge for creating microarrays and the like. The microdeposition pin may be used either alone or with a plurality of microdeposition pins in conjunction with a holder. The concave edge of the pin is especially adapted for helping to control the spreading of a deposited material. By selectively controlling the spread of the reagent composition from the microdeposition pin, the flow of the reagent composition from the deposition target area may be reduced. Sensor strips having raised substrate features with limited or no spreading of the reagent composition beyond the target area are disclosed.

24 Claims, 10 Drawing Sheets

(51) Int. Cl.
*B01L 3/02* (2006.01)
*G01N 35/10* (2006.01)

(56) References Cited

U.S. PATENT DOCUMENTS

| | | | |
|---|---|---|---|
| 6,594,432 | B2 | 7/2003 | Chen et al. |
| 6,935,727 | B2 | 8/2005 | DaQuino et al. |
| 6,936,461 | B2 | 8/2005 | Gagna et al. |
| 6,977,722 | B2 | 12/2005 | Wholstadter et al. |
| 7,005,293 | B2 | 2/2006 | DaQuino et al. |
| 7,128,398 | B2 | 10/2006 | DaQuino et al. |
| 2002/0094304 | A1* | 7/2002 | Yang et al. .................. 422/100 |
| 2003/0003025 | A1* | 1/2003 | MacAulay et al. .......... 422/100 |
| 2003/0112295 | A1 | 6/2003 | DaQuino et al. |
| 2003/0113729 | A1 | 6/2003 | Da Quino et al. |
| 2005/0052646 | A1 | 3/2005 | Wohlstadter et al. |
| 2005/0142033 | A1 | 6/2005 | Glezer et al. |
| 2006/0028509 | A1 | 2/2006 | DaQuino et al. |
| 2006/0038536 | A1 | 2/2006 | LaFollette et al. |
| 2006/0056904 | A1 | 3/2006 | Haselton et al. |
| 2006/0183131 | A1 | 8/2006 | Toporik et al. |
| 2006/0246443 | A1 | 11/2006 | Bockelmann et al. |
| 2006/0257896 | A1 | 11/2006 | Pollock et al. |
| 2006/0263786 | A1 | 11/2006 | Sorek et al. |
| 2007/0031960 | A1 | 2/2007 | Dosmann et al. |
| 2007/0059769 | A1 | 3/2007 | Blixt et al. |
| 2007/0133281 | A1 | 6/2007 | Fujita et al. |
| 2007/0259386 | A1 | 11/2007 | Toporik et al. |
| 2007/0265170 | A1 | 11/2007 | Blixt et al. |
| 2007/0281865 | A1 | 12/2007 | Blixt et al. |
| 2008/0014590 | A1 | 1/2008 | Dahary et al. |
| 2008/0019968 | A1 | 1/2008 | Blixt et al. |
| 2008/0063794 | A1 | 3/2008 | Krotz et al. |
| 2008/0069962 | A1 | 3/2008 | Light et al. |
| 2008/0156662 | A1 | 7/2008 | Wu et al. |
| 2008/0159913 | A1 | 7/2008 | Jung et al. |
| 2008/0279727 | A1* | 11/2008 | Haushalter .................... 422/100 |

FOREIGN PATENT DOCUMENTS

| | | | |
|---|---|---|---|
| WO | WO 9934214 A1 * | 7/1999 | ........... G01N 33/543 |
| WO | WO 02051549 | 7/2002 | |
| WO | WO 03086631 | 10/2003 | |
| WO | WO 2005001476 | 1/2005 | |
| WO | WO 2005105309 | 11/2005 | |
| WO | WO 2007087449 | 8/2007 | |

OTHER PUBLICATIONS

Nabeel Affara, "Resource and Hardware Options for Microarray-Based Experimentation", "Briefings in Functional Genomics and Proteomics", Apr. 2003, pp. 7-20, vol. 2, No. 1, Publisher: Henry Stewart Publications.

Thompson, et al., "It's easy to build your own microarrayer!", "TRENDS in Microbiology", Apr. 4, 2001, pp. 154-156, vol. 9, No. 4, Publisher: Elsevier Science Ltd.

Tsai, et al., "Silicon Microarray Pin with Selective Hydrophobic Coating", "International Mechanical Engineering Congress", ~Nov. 2004, Publisher: ASME, Published in: US.

Affara, "Special Issue Papers Resource and hardware options for microarray-based experimentation", Apr. 2006, pp. 7-20, vol. 2, No. 1, Publisher: Henry Stewart.

Mukhopadhyay, "The versatility of microarrayers", "Analytical Chemistry", Sep. 1, 2006, pp. 5969-5972, Publisher: American Chemical Society.

Website, "Microarray 946 Printing Technology", Downloaded Jan. 29, 2007 Publisher: http://arrayit.com/Products/Printing/946/946.html.

Website, "Microarray Stealth Spotting Pins and Printheads", Downloaded Jan. 29, 2007, Publisher: http://arrayit.com/Products/Printing/Stealth/stealth.html.

* cited by examiner

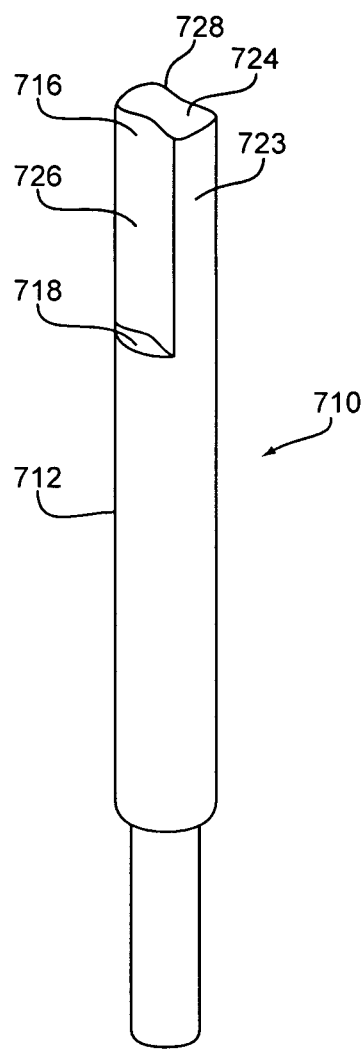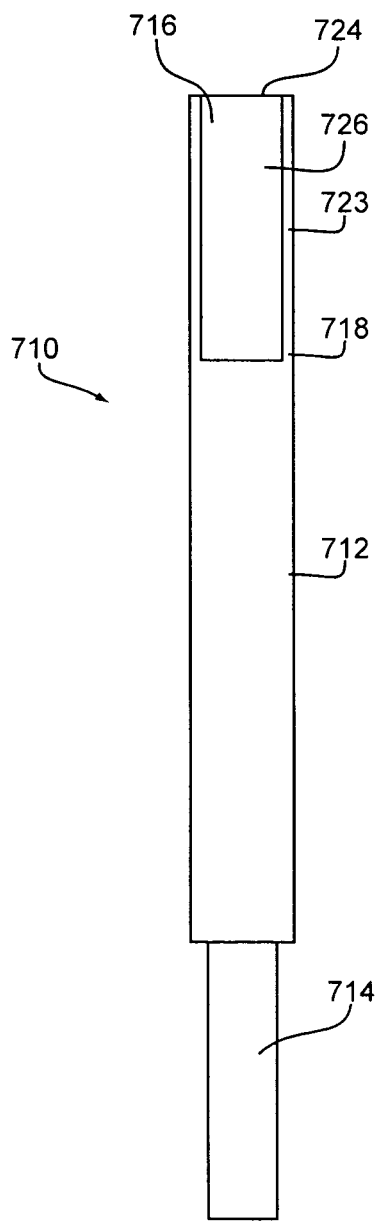
Fig.13A
Fig.13B

US 9,182,393 B2

MICRODEPOSITION SYSTEM FOR A BIOSENSOR

REFERENCE TO RELATED APPLICATIONS

This application claims the benefit of U.S. Provisional Application No. 60/942,437 entitled "Microdeposition System For A Biosensor" filed Jun. 6, 2007, which is incorporated by reference in its entirety.

BACKGROUND

Microarray biosensors for biological analysis are well known in the art. Generally, a biochemical substance, such as multiple droplets of a reagent, is deposited onto a substrate to form the microarray. Each droplet of the reagent is preferably in electrical communication with an electrode so as to form an individual biosensor. The droplet of reagent may then be exposed to a biological agent or the like, such that a reaction is caused. With the aid of at least one additional electrode, various factors of the reaction may be measured and/or observed to provide the analysis.

Various techniques may be used to create the microarray biosensors, such as screen printing, ink-jetting, micro-pipetting, and pin-deposition. Each of the techniques have advantages. For instance, screen printing may be preferred when a relatively large deposit of a thick reagent layer is required to control spreading of the reagent composition. "Spreading" refers to the outward flow of a deposit of material due to the material's viscosity. Screen printing also may be preferred due to the high speed at which deposition may occur. If smaller area deposits are desired, ink-jetting, micro-pipetting, or pin-deposition may be preferred. These techniques can more precisely control the volume of a reagent composition deposited onto a substrate.

In contrast to screen printing, ink-jetting and micro-pipetting are non-contact techniques, where only the reagent composition contacts the substrate. While ink-jetting can deposit very small volumes of the reagent composition with little spreading, the method cannot effectively deposit biomolecules due to the small size of the individual droplets sprayed by the print head, approximately 10 to 100 picoliters (pL). Furthermore, biomolecules, especially those of high molecular weight, may lead to clogging of the deposition nozzle. Micro-pipetting can deposit very small volumes of the reagent composition, but spreading is influenced by the flow of the reagent composition liquid over the topography of the substrate. If the substrate has raised areas formed by conductors or other features, the reagent composition may flow from the raised areas into lower areas providing more undesirable spreading from the deposition area. As with ink-jetting, biomolecules in the reagent composition also may clog the pipette.

With pin-deposition, one or more microdeposition pins contact the substrate to transfer the reagent composition. Pin contact with the substrate allows for the transfer of relatively small volumes of reagent composition while reducing spreading of the reagent composition from raised features. Thus, pin-deposition may provide thin reagent layers from small deposition volumes while maintaining liquid control advantages.

Pin-deposition generally starts by lowering multiple pins into a source plate having wells containing a reagent composition. As the pins are dipped into the wells, they are coated with the reagent. The pins are moved above the substrate, and the reagent is transferred from the pins to the substrate during a brief touchdown. Pin-deposition also allows the force with which the pin contacts the substrate to be altered.

Conventional deposition pins generally are quill or solid in design. Quill pins differ from solid pins in that quill pins include a narrow slit at the tip of the pin. This slit acts as a fluid reservoir, which holds the reagent composition before the pin contacts the substrate. Each time a quill pin contacts the substrate, it deposits at least a portion of the reagent composition from the reservoir. The reservoir is generally sized to hold sufficient volume of reagent for multiple depositions.

Solid microdeposition pins generally have small, flat tips that are dipped into the reagent composition before each contact with the substrate. As the reagent composition flows down the exterior sides of the pin, there is no passageway for biomolecules and other high molecular weight constituents to clog. The volume and morphology of the resulting deposition spot may depend on the diameter of the solid pin tip, the surface tension of the reagent composition, and the hydrophobic character of the substrate in relation to the hydrophilicity of the reagent composition. For example, a 0.2 millimeter (mm) diameter pin may produce depositions having a diameter of approximately 400 micrometers ($\mu$m). When depositing solution volumes of from 10 picoliters (pL) to 10 nanoliters (nL), the 0.2 mm diameter pins may provide deposition areas having diameters ranging from 100 $\mu$m to 1,000 $\mu$m. Conventional solid pins having tips that are either round or square are known to produce substantially round deposition areas.

However the biosensors are manufactured, they may be used for analysis of a biological fluid, such as whole blood, urine, or saliva. Typically, biosensors have a measurement device that analyzes a sample of the biological fluid placed on a sensor strip. The analysis may determine the concentration of one or more analytes, such as alcohol, glucose, uric acid, lactate, cholesterol, or bilirubin, in the biological fluid. The analysis is useful in the diagnosis and treatment of physiological abnormalities. An ongoing need remains for microdeposition techniques that provide enhanced control over the spreading of the deposited reagent composition.

SUMMARY

A microdeposition system includes one or more microdeposition pin with a polygonal cross-section contact surface and one or more concave or substantially flat exterior edge. The microdeposition pins reduce or alter the spreading of a reagent composition away from the concave and/or substantially flat exterior edges of the pin. The pins also may reduce or alter the amount of the reagent composition that flows past an imaginary line extending between adjacent edges of a concave edge of the pin.

A microdeposition pin for microprinting includes a shaft terminating in a head having a polygonal cross-section with at least one concave exterior surface. The pin may have at least two concave exterior surfaces, at least three concave exterior surfaces, at least two concave exterior surfaces and at least two convex exterior surfaces, or at least one substantially flat exterior surface. The concave exterior surface may form an external reagent composition reservoir. The cross-sectional area of the concave exterior surface may be less at the head than higher on the shaft. The concave exterior surface of the pin may extend from about 2 mm to about 8 mm from the head along a longitudinal direction of the shaft, and the shaft may taper toward the head, the shaft and the head may have substantially the same radius.

The microdeposition pin may have a maximum cross-sectional head diameter from about 0.25 mm to about 3 mm or from about 0.3 mm to about 1.5 mm. A radius having a length from about 1 mm to about 4 mm may define the arc of the concave exterior surface of the head. The cross-section of the head may include at least two convex and at least two concave exterior surfaces, where the cross-section of the head has a maximum diameter from about 0.25 mm to about 2.8 mm and a minimum distance from about 0.1 mm to about 1.5 mm. The cross-section of the head also may include at least two convex and at least two concave exterior surfaces, the cross-section of the head having a ratio of the maximum diameter to the minimum distance of from 30 to 0.17. The cross-section of the pin head may have a maximum diameter from about 2 mm to about 3 mm, a minimum distance from about 1 mm to about 1.5 mm, and a maximum arc distance from about 1.3 mm to about 1.4 mm, where a radius defines the arc of the concave exterior surface and the radius has a length from about 3 mm to about 4 mm.

A microdeposition pin also may include a shaft terminating in a head having a polygonal cross-section with at least one convex exterior surface and at least one substantially flat exterior surface. The pin may have at least three substantially flat exterior surfaces or may have at least two convex exterior surfaces and at least two substantially flat exterior surfaces. The substantially flat exterior surface may extend from about 2 mm to about 8 mm from the head of the microdeposition pin along a longitudinal direction of the shaft. The shaft may taper toward the head or the shaft may have substantially the same radius as the head. The pin may have a maximum cross-sectional head diameter from about 0.25 mm to about 3 mm or from about 0.3 mm to about 1.5 mm. The cross-section of the head may include at least two convex and at least two concave exterior surfaces, where the cross-section of the head has a maximum diameter from about 0.25 mm to about 2.8 mm and a minimum distance from about 0.1 mm to about 1.5 mm. The cross-section of the head also may include at least two convex and at least two concave exterior surfaces, the cross-section of the head having a ratio of the maximum diameter to the minimum distance of from 30 to 0.17.

A biosensor may include a substrate having at least one raised feature and at least one reagent composition deposition on the raised feature, the deposition including an active biomolecule having a weight average molecular weight from about 10,000 to about 500,000, where the spread of the reagent composition beyond the raised feature is at most 0.3 mm. The deposition may include an active biomolecule having a weight average molecular weight from about 100,000 to about 400,000, and the active biomolecule may include an active enzyme. The active enzyme may include amine functional groups capable of hydrogen bonding interactions. The substrate may be plastic and may include raised features having an average height above a top surface of the substrate of from about 5 μm to about 25 μm or of at most 5 μm.

The raised feature of the biosensor may be rectangular in shape as may be the deposition. The deposition may be non-circular in shape. The raised feature may be electrically conductive and the deposition may span from about 0.5 mm to about 3 mm of the longitudinal length of the raised feature. The raised feature may have a width of at most 1.5 mm or may have a width of from about 0.2 mm to about 1.2 mm. The average thickness of the deposition may be from about 1 μm to about 2 μm and may include from about 0.02 μL to about 5 μL of the reagent composition. The maximum length of the deposition may be from about 0.15 mm to about 3.2 mm or may be from about 0.6 mm to about 1.0 mm. The deposition may include at least one binder having a weight average molecular weight from 10,000 to about 900,000 and may spread beyond the raised feature by at most 0.15 mm. The deposition may have a substrate spread of at most 20%, of at most 8%, from 1% to 4%, from 1% to 2%, or essentially 0%.

A method of making a biosensor includes forming at least one raised feature on a substrate and depositing at least one reagent composition on the raised feature, the reagent composition including an active biomolecule having a weight average molecular weight from 10,000 to 500,000, where the spread of the reagent composition beyond the raised feature during the depositing is at most 0.3 mm. The depositing may include contacting at least one microdeposition pin to the raised feature. The deposition pin may be one of the deposition pins previously discussed. The percent spread distance of the reagent composition from an exterior arc line of the microdeposition pin during the depositing may be from about 5% to about 15% or from about 5% to about 10% with respect to the length of the exterior arc line.

The depositing may include contacting at least one microdeposition pin having a polygonal cross-section with at least one concave surface to the raised feature. The depositing may include contacting at least one microdeposition pin having a polygonal cross-section with at least one convex and at least one substantially flat surface to the raised feature. The deposited reagent composition may have a viscosity from about 1 cp to about 100 cp or from about 1 cp to about 20 cp. The depositing may include flowing the reagent composition on an exterior surface of the microdeposition pin, channeling the reagent composition toward a center of the microdeposition pin, forming an initial deposition site on the substrate, and/or configuring an initial deposition site in response to an exterior surface of the microdeposition pin.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the claims that follow.

BRIEF DESCRIPTION OF THE DRAWINGS

The invention can be better understood with reference to the following drawings and description. The components in the figures are not necessarily to scale, emphasis instead being placed upon illustrating the principles of the invention.

FIGS. 7-13B illustrate alternate embodiments of microdeposition pins of the present invention.

DETAILED DESCRIPTION

A microdeposition system for a biosensor has one or more microdeposition pins with contact surfaces having a polygonal cross-section and one or more concave exterior edges. The microdeposition pins reduce the spreading of a reagent composition away from the concave edge in relation to substantially flat or convex exterior edges. Microdeposition systems with microdeposition pins having polygonal contact surfaces and one or more substantially flat exterior edge also reduce the spreading of the reagent composition away from the substantially flat edges in relation to convex exterior edges. Thus, in addition to size and reagent composition morphology, the shape of the contact surface of the microdeposition pin may be used to alter spreading of the reagent composition. Contact surfaces having concave edges also may provide external reagent composition reservoirs to a solid microdeposition pin.

The present invention will be discussed with reference to creating a biosensor by depositing a reagent composition. However, the present invention is equally adaptable to forming most microarrays created using microdeposition.

Figure 1:
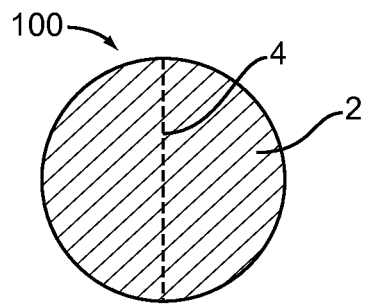
FIG. 1 represents a cross-section of a contact surface of a conventional round microdeposition pin.

Conventional contact surface 2 of pin 100 used in pin-deposition is illustrated in FIG. 1. Pin 100 has a circular contact surface 2, known to create substantially circular footprints when employed during pin-deposition. A further discussion regarding the resultant footprint of the contact surface 2 will be discussed below.

Figure 3A:
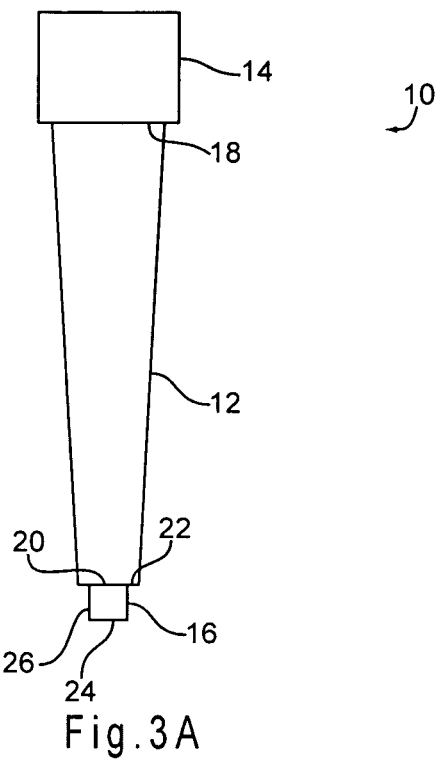
FIG. 3A illustrates an embodiment of a microdeposition according to the present invention.
Figure 3B:
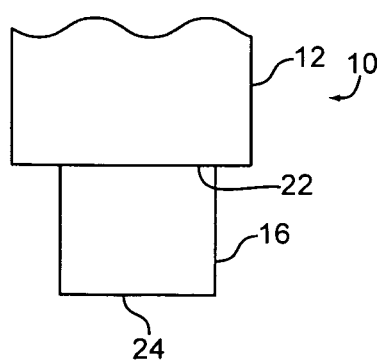
FIGS. 3B-3C are illustrations of a partial side view and bottom view, respectively, of the embodiment of FIG. 3A.
Figure 3C:
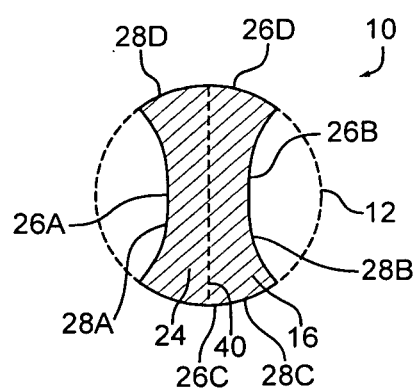

As shown in FIGS. 3A-3C, a first aspect of the present invention includes a microdeposition pin 10 having a shaft 12, a mounting collar 14, and a head 16. The shaft 12 is illustrated having a tapered cross-section extending from a first end 18 of the shaft to a second end 20. But the shaft 12 may also have a constant radius throughout its length or may have other geometric cross-sections throughout its length without deviating from the scope of the present invention. Thus, the radius of the shaft 12 may remain substantially constant, may change constantly to provide a taper, or may change abruptly, as illustrated in FIG. 3A.

The collar 14 is attached to the first end 18 of the shaft 12 and extends outwardly therefrom. The collar 14 may be integrally formed with the shaft 12 or attached thereto using methods known to those in the art. The collar 14 may be employed to connect the pin 10 to a holder, as will be discussed below.

As shown in FIG. 3A, the head 16 of the pin 10 extends outwardly from the second end 20 of shaft 12. The head includes a base 22, a contact surface 24 and side surfaces 26. The base 22 is in communication with the shaft 12, while the contact surface 24 is remote from the shaft.

Figure 2:
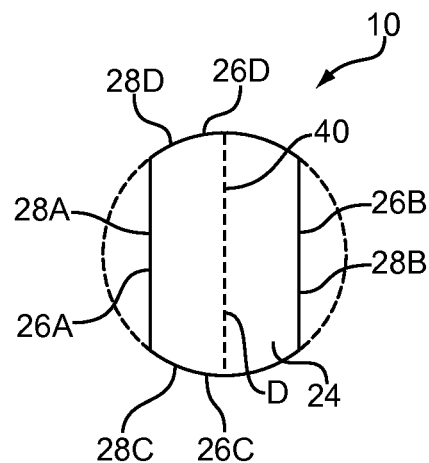
FIG. 2 represents a cross-section of a deposition pin having the same maximum diameter as the pin of FIG. 1, but with two substantially flat surfaces and two convex surfaces.

A more detailed illustration of head 16 will be discussed with reference to FIGS. 2 and 3B-3C. As previously mentioned, the head 16 includes a base 22, a contact surface 24 and side surfaces 26. The side surfaces 26, which include first side wall 26A, second side wall 26B, third side wall 26C and fourth side wall 26D, extend between the base 22 and contact surface 24 thereby connecting the two. As shown in FIGS. 2 and 3B-3C, the side walls 26A-26D may be substantially vertical.

The side walls 26A-26D abut the contact surface 24 at edges 28A-28D, respectively. The edges 28A-28D define the outer boundary of contact surface 24. As shown in FIG. 3C, edges 28A and 28B are concaved, while edges 28C and 28D are convexed. As shown in FIG. 2, edges 28A and 28B are substantially flat, while edges 28C and 28D are convexed. The concave or substantially flat edges 28A and 28B help control the flow of biochemical material as the head 16 of the pin 10 contacts a substrate.

The contact surface 24 of pin 10 has a maximum diameter D, illustrated by dotted line 40, passing through the center of the surface. The maximum diameter D is the distance between the two farthest points positioned on the perimeter of a cross-section of the contact surface 24.

Figure 4:
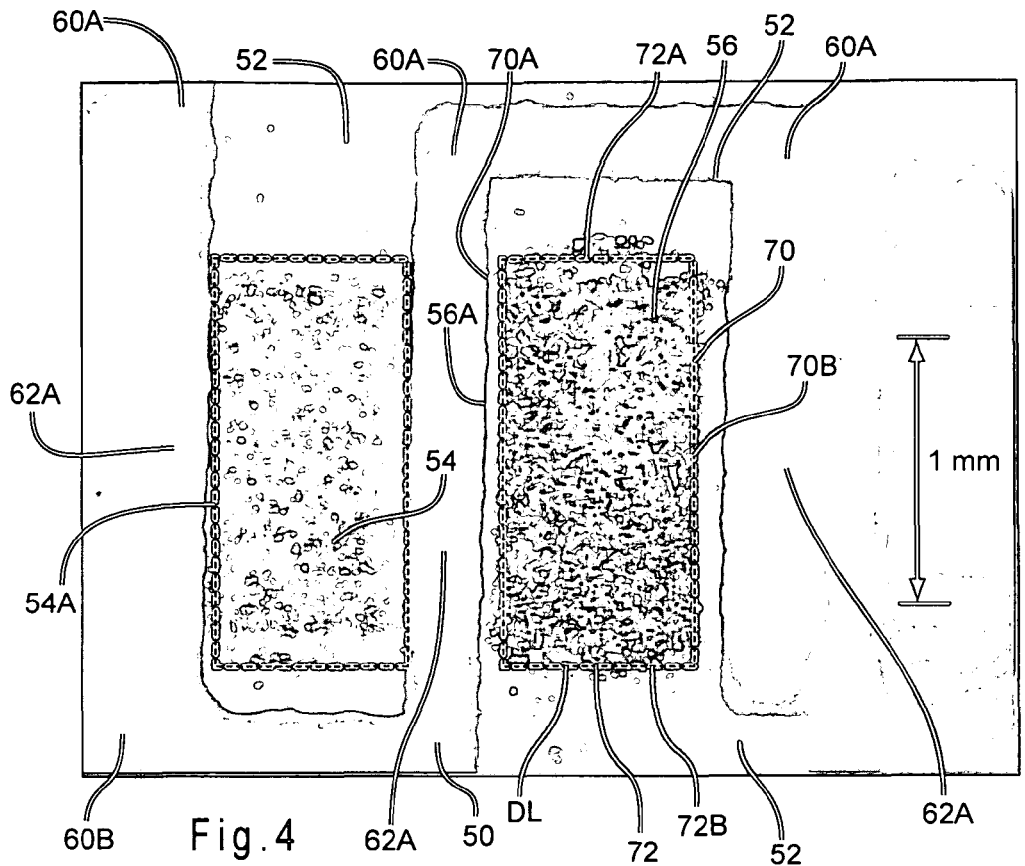
FIG. 4 is a top view of an image depicting reagent composition depositions made using the microdeposition pin of FIG. 3A.

FIG. 4 illustrates the deposition result when using a reagent with the pin 10 of FIG. 3C described above in conjunction with a substrate 50. The contact surface of the pin used to create the deposition result of FIG. 4 had a maximum diameter of approximately 2.4 mm. The substrate 50 includes electrical conductors 52 defining a first target area 54 and a second target area 56 separated by portions of the substrate 50. The top and bottom portion of the electrical conductors in each of the first target area 54 and second target area 56, as well as portions 60A and 60B of the substrate 50, positioned adjacent the top and bottom of the conductors 52 in FIG. 4 were masked with a layer of dielectric to limit exposure at locations where the reagent spreading was not critical. In contrast, portions 62A of the substrate that are more centrally located relative to the targets areas 54, 56 and are critical areas, were not encumbered by a dielectric layer. The criticality of the locations is dependent on whether target areas are adjacent to one another. For instance, the side 54A of first target area 54 and the side 56A of second target area 56 are critical because only a portion of the substrate 50 separates the conductors 52 in each target area 54, 56. If the reagent was allowed to flow past the substrate 50 and electrically connect the first target area 54 to the second target area 56, the sensor would be less effective.

The spreading of the reagent proximate the portions 62A of the substrate 50 after deposition is controlled by the concave edges 28A and 28B of the pin 10. The convex edges 28C and 28D at the top and bottom of the head 16 of the pin 10 of FIG. 3C resulted in more reagent composition spreading along the conductors 52 as compared to the concave edges 28A and 28B.

A discussion of how the concave edges 28A, 28B of the head 16 of the pin 10 help limit the outward spread of the reagent material such that a more controlled footprint can be achieved is illustrated with reference to second target area 56 illustrated in FIG. 4. The second target area 56 includes a dotted rectangular line DL having a first set 70 of opposing side walls 70A and 70B along with a second set 72 of opposing side walls 72A and 72B. The dotted line defines a desired location for the deposit of reagent deployed by pin 10. As the pin 10 contacts the conductor 52 to deposit the reagent the concave edges 28A and 28B are positioned adjacent and between the first set 70 of opposing side walls 70A, 70B. And the convex edges 28C, 28D of the head 16 are positioned adjacent and between with the second set 72 of opposing side walls 72A, 72B.

As can be viewed in FIG. 4, adjacent the first set 70 of side walls 70A, 70B the reagent does not flow past the dotted line DL due to the shape of the concave edges. Further, the reagent actually forms a substantially straight line adjacent the location of where the concave edges 28A, 28B contacts the conductor 52. In contrast, the reagent that is deposited adjacent the convex edges 28C, 28D tends to flow past the second set 72 of side walls 72A, 72B of dotted line DL.

In fact, the reagent composition did not spread from the conductors 52 onto the substrate 50 adjacent the first set 70 of side walls 70A, 70B. This reduction in spreading was observed even as the maximum diameter of the pins increased from about 1.6 to about 2.4 mm to provide a longer deposition area along a conductor. Thus, the spreading of the reagent composition from raised rectangular features—the conductors 52—of the substrate 50 may be controlled using deposition pin heads that include a concave edge along its contact surface.

This is particularly evident when comparing the reagent footprint of FIG. 4 created using pin 10 of FIG. 3C to a footprint made using a conventional pin head. For example, conventional pin 100 of FIG. 1 was used to create the reagent footprints of FIG. 5. The reduction in spreading provided by the concave edge may also be seen from the reagent footprint of FIG. 6, which was made with a pin having substantially flat edges, such as seen in FIG. 2. It should be noted that the contact surface 2 of pin 100 (FIG. 1) has a maximum diameter 4 that is substantially equal to the maximum diameter 40 of the contact surface 24 of pin 10 (FIGS. 2 and 3c). And in all three scenarios the reagent composition deposited had a viscosity from about 2 to about 20 centipoise (cp), as determined with a Brookfield Model DV3 Viscometer equipped with an ULA assembly for measuring reagent compositions having viscosities lower than 300 cp. Viscosity measurements were performed at room temperature with the instrument temperature set to 25° C. The measurements were performed at shear rates of 50, 100, 200 and 300 cps (cycle per second) to provide an indication of whether the composition is sheared thin or thick. A 100 mM phosphate buffer solution was used as a control, which typically gave viscosity readings in the range of about 1 to about 1.3 cp under different shear rates.

Figure 5:
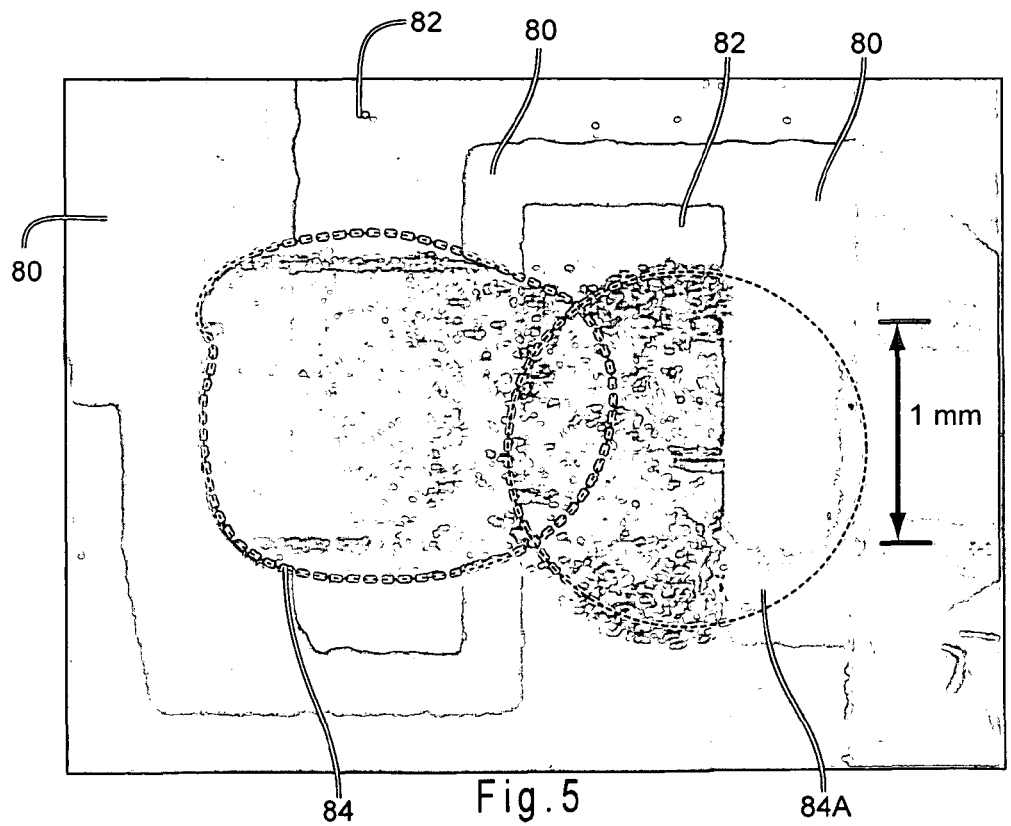
FIGS. 5-6 are images depicting reagent composition depositions made using the microdeposition pins of FIGS. 1 and 2, respectively.
Figure 6:
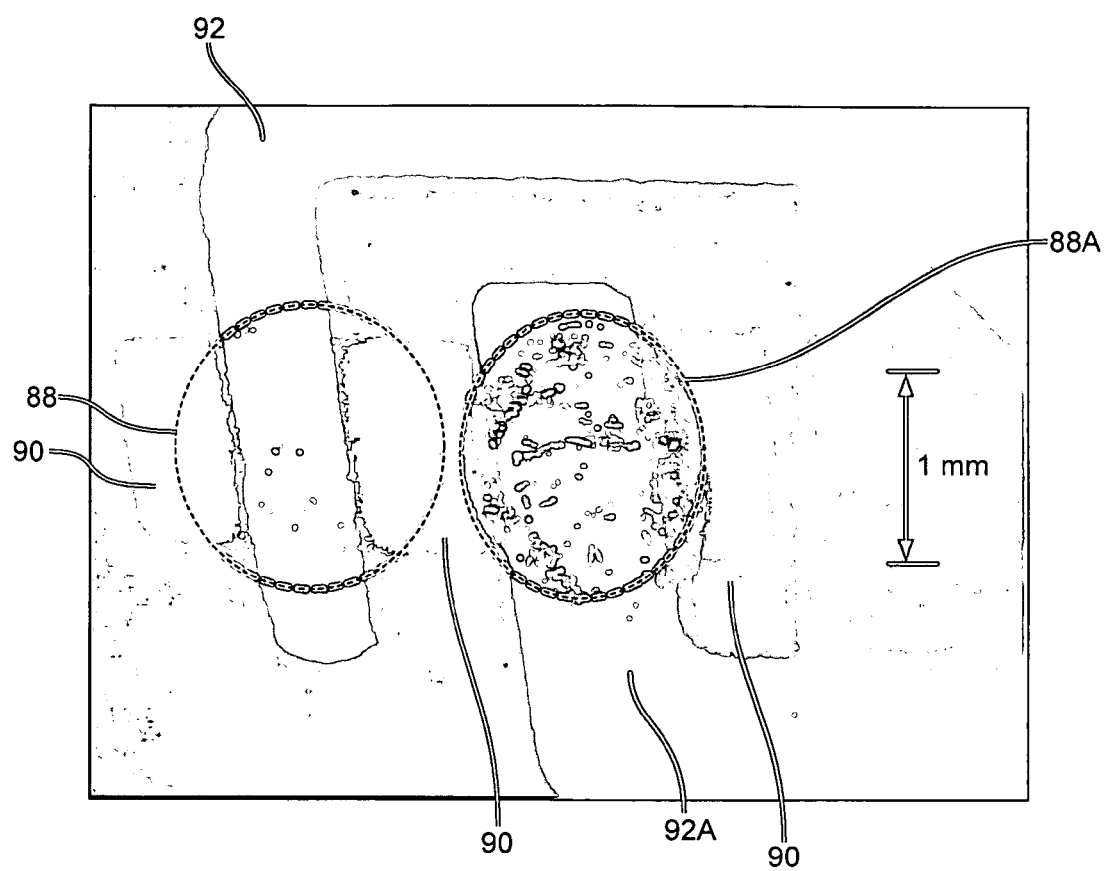
Figure 7:
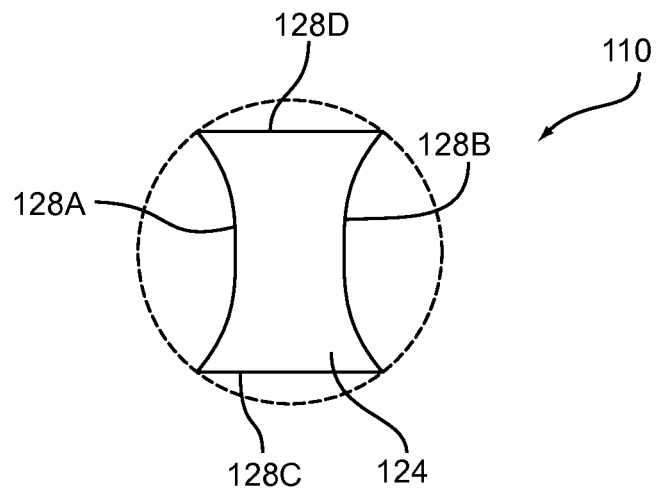

With attention to FIG. 5 it can be viewed that the substantially circular contact surface 2 of pin 100 left a first footprint 84 and a second footprint 84A that are substantially circular. Each footprint 84, 84A is highlighted by a dotted line. As a result of the reagent spreading, both of the footprints 84, 84A spread across a portion of the substrate 80 and into contact with one another, thereby corrupting the sensor. Similarly, as shown in FIG. 6, the footprints 88, 88A created using pin of FIG. 2 also spread from conductors 92, 92A to a portion of a substrate 90.

By selectively controlling the spread of the reagent composition away from the microdeposition pin, the flow of the reagent composition away from the deposition target area may be reduced. Thus, biosensors may include sensor strips having raised substrate features with limited or no spreading of the reagent composition beyond the features. The sensor strips may have substantially rectangular shaped depositions of a reagent composition including active biomolecules on the features. The raised substrate features may be conductors providing electrical communication between the sample and the measurement device.

Figure 8:
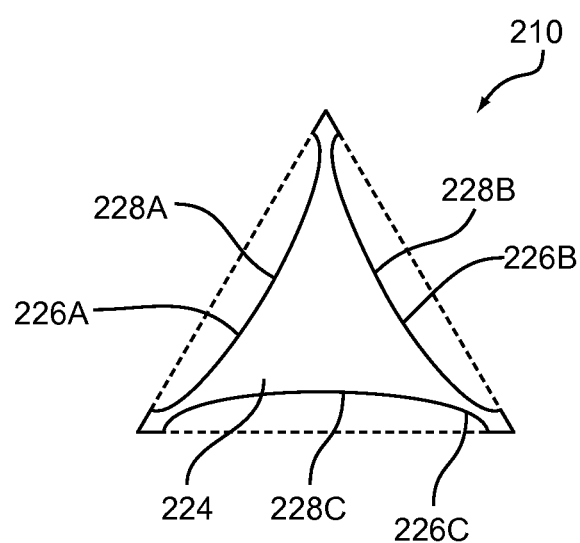

As shown in FIGS. 7-10, the head of the pin may have many different shapes. For example in FIG. 7, the contact surface 124 of the pin 110 includes first and second concave edges 128A, 128B and adjacent straight edges 128C, 128D. As mentioned with regard to FIG. 2, the straight edges tend to leave reagent footprints that are arcuate. FIG. 8 illustrates a pin 210 with a contact surface 224 having a substantially triangular shape defined by three concave edges 228A, 228B and 228C. The edges 228A, 228B and 228C are defined by the intersection of each sidewall 226A, 226B and 226C and contact surface 224.

Figure 9:
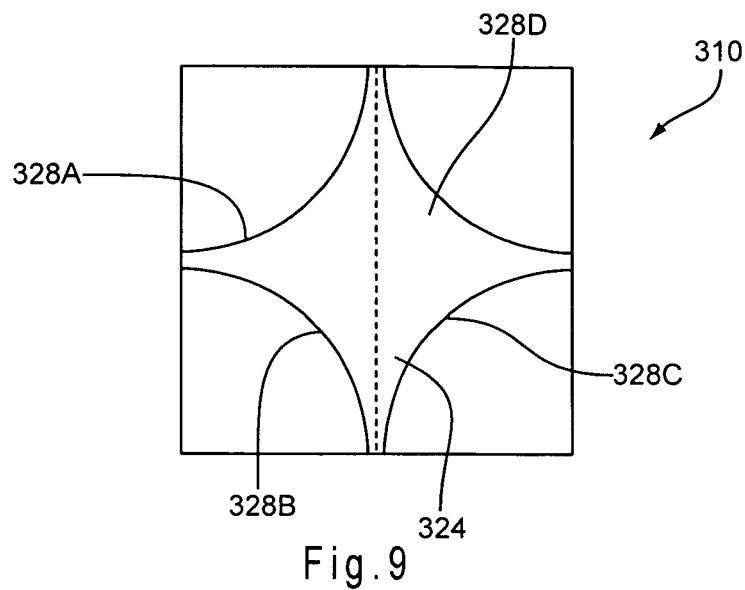
Figure 10:
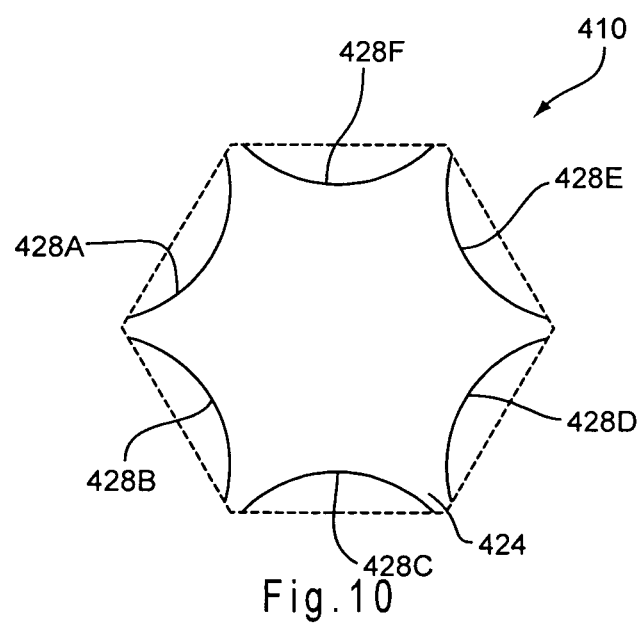

FIGS. 9 and 10 illustrate pins 310, 410 having contact surfaces 324, 424 that have other polygonal shapes. In pin 310 the contact surface 324 has four concave edges 328A, 328B, 328C and 328D. And in pin 410, the contact surface 424 includes concave edges 428A-428F. Although not shown in the figures, the contact surface of a pin may have any combination of concave edges, straight edges, convex edges or other geometric shapes that include at least one concave edge without deviating from the scope of the present invention.

Figure 11:
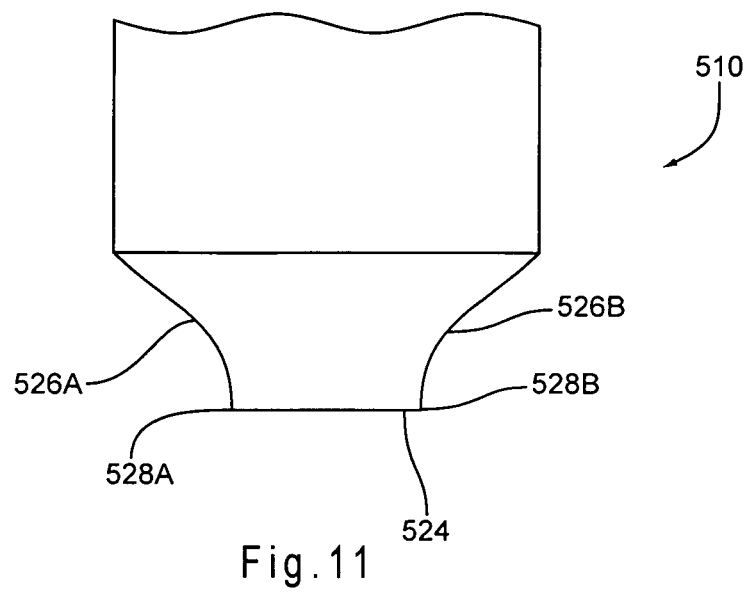

Further, although the side walls of each of the pins have been illustrated as substantially vertical, the side walls may be slanted and/or concaved. For example, with reference to FIG. 11, pin 510 includes a contact surface 524 intersecting with slanted concave walls 526A, and 526B. Each of the side walls 526A, 526B intersect the contact surface 524 at a concave edge 528A, 528B. Although the side walls are illustrated as slanting outwardly they may slant inwardly. Once again, any combination of slanted and/or concaved walls, as well as convexed side walls may be employed without deviating from the scope of the invention.

Figure 12:
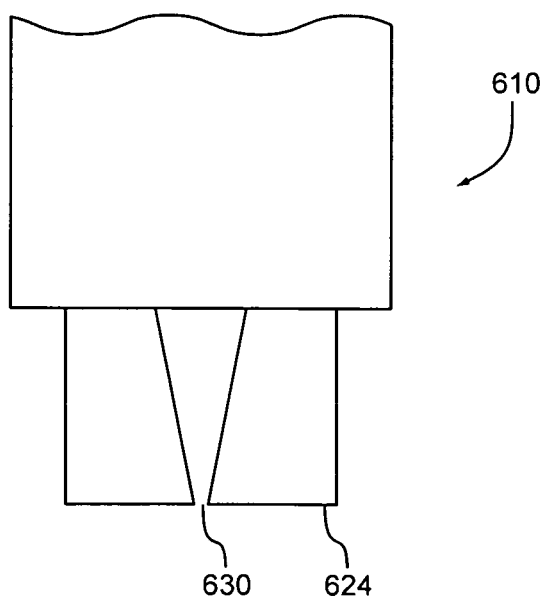

As shown in FIG. 12, a pin 610 may include a contact surface 624 and a sample channel 630 for acting as a reservoir. The sample channel 630 may be created and employed using methods known to those in the art.

Concave edges/side walls as well as sidewalls reduce the spread of the reagent composition. They may be selected to reduce the spread of the reagent composition to form an essentially straight edged or other shaped reagent composition deposition on a sensor strip. They also may act as a reservoir for the reagent composition. By providing the micro-deposition pin with one or more concave exterior edges, the spread of the reagent composition away from the concave edge may be reduced in relation to the spread of the reagent composition away from convex or substantially flat edges.

When a microdeposition pin contacts the substrate, the effect of gravity and the surface tension of the reagent composition cause the composition to flow along the surface of the pin and onto the substrate. The composition forms an initial deposition area on the substrate. Due to surface tension and gravity, the reagent spreads outward from the initial deposition site to form a more spherical shape on the substrate. The reagent spreads outward from the initial deposition site until the reagent essentially dries or solidifies. The flow of the reagent may stop before drying or solidification is complete because of the increasing viscosity of the reagent composition due to drying or solidification, or due to a balancing of the surface energy of the reagent composition.

The viscosity of the reagent composition may be selected to alter the spread from the initial deposition site. However, competing effects are involved. As the viscosity of the reagent composition increases, the flow rate of reagent composition from the microdeposition pin to the substrate may decrease, while the volume of reagent composition transferred to the substrate may increase due to a larger drop of the higher viscosity composition adhering to the microdeposition pin. Thus, a lower reagent composition flow rate may require longer touchdown times of the pin to the substrate to obtain a similar amount of reagent composition deposition on the substrate while if a larger volume of the reagent composition adheres to the pin, a shorter touchdown time may suffice.

Flat and concave edges guide the reagent toward the center of the pin. The flat and concave surfaces also may guide the reagent to form an initial deposition area with a shape responsive to the configuration of the contact surface of the pin. When the reagent composition is guided more toward the center of the pin, the spreading of reagent on the substrate starts from a smaller and/or shaped initial deposition site, thus reducing or controlling the spread of the reagent composition on the substrate. The shape of the initial deposition site may be controlled by the shape of the microdeposition pin's contact surface, e.g., a triangular contact surface makes a triangular footprint. Then, as the reagent flows on the substrate from the pin, the reagent composition "fills" in the concave portions and may provide a deposition having substantially straight edges.

FIGS. 13A-13B illustrate a perspective and side view, respectively of a microdeposition pin 710 having a shaft 712, a mounting collar 714, and a head 716. Unlike the pin 10, the mounting collar 714 is of smaller radius than the shaft 712 to which it is attached. The head 716 includes convex side wall 723 having a smaller radius than shaft 712. The head 716 also includes a concave side wall 726.

The concave side wall 726 extends from the contact surface 724 to a first end 718 of the shaft 712. The concave side wall 726 may extend any distance from the contact surface 724 to the shaft 712 or may end somewhere along the longitudinal axis of the head 716 either gradually or abruptly. For example the concave side wall 726 may longitudinally extend from about 2 mm to about 8 mm, and more preferably about 6 mm, from the contact surface 724 to the shaft 712. The length and angle of the arc of the concave side wall 726 may remain constant or may decrease or increase when approaching the contact surface 724 and hence concave edge 728. When the length of the arc of the concave side wall 726 decreases toward the contact surface 724, a smaller cross-sectional concave edge is provided. And the concave side wall 726 may retain more reagent composition farther from the contact edge 728. In this manner, a larger external reservoir for the reagent composition may be created, while the desired ratio of concave to convex cross-sectional diameters may be maintained.

Figure 14:
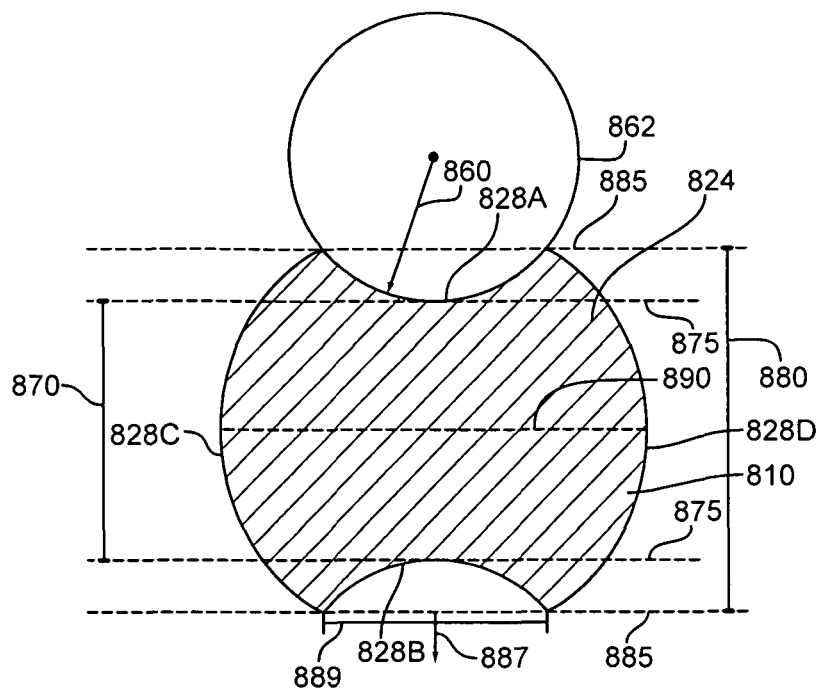
FIG. 14 is a schematic diagram of an embodiment of a contact surface of a pin according to the present invention.

FIG. 14 illustrates a cross-section of a contact surface 824 of a pin 810 having a maximum diameter 890 with the two concave edges 828A, 828B and the two convex edges 828C, 828D. Radius 860 of circle 862 defines an arc of the concave edges 828A, 828B. Other arcs may be used. A minimum distance 870 is the distance between interior arc lines 875 and defines the closest portions of the arcs of the concave edge 828A, 828B. Maximum arc distance 880 is the distance between exterior arc lines 885 and defines the farthest portions of the arcs of the concave edges 828A, 828B. For example, a microdeposition pin tip may have a cross-sectional maximum diameter of about 2.4 mm. The radius defining the arc of the concave surface may be from about 1.2 mm to about 5 mm. A radius of about 5 mm may provide substantially flat exterior edges. For concave edges, a radius from about 1 mm to about 4 mm may be preferred. When the cross-sectional maximum diameter of the microdeposition pin tip is about 2.4 mm and the radius defining the arc of the concave edges is about 3.7 mm, the microdeposition pin may have a minimum distance of about 1.1 mm and a maximum arc distance of about 1.3 mm to about 1.4 mm. While a particular configuration of the tip is shown, the tip may have other configurations including those with different or asymmetrical cross-sections and those having one or more concave exterior edges.

When depositing the reagent composition on a substrate, the spread of the reagent composition in a direction perpendicular to the curvature of a concave edge may be reduced. The concave edges may be configured to control the spread of the reagent composition to obtain a desired edge or shape of the deposition on the substrate of a sensor strip. While particular concave edges are shown, the concave edge may have other configurations including angular, curvilinear, a combination thereof, or the like. Spread distance 887 is the distance the reagent composition spreads outward from the exterior arc line 885 when deposited on the substrate. The spread distance 887 may be expressed in terms of length, percent, or the like. The percent spread may be the percentage of the spread distance 887 over arc distance 889 as defined between the ends of the arcs along the exterior arc line 885. Preferable percent spreads for the reagent composition are from about 5% to about 15% and more preferably from about 50% to about 100%. Other percent spread distances may be used.

The microdeposition pins may have a maximum cross-sectional contact surface diameter from about 0.25 mm to about 3 mm and preferably from about 0.3 mm to about 1.5 mm. Other maximum cross-sectional diameters may be used. When the cross-section of a pin's contact surface includes at least two convex and at least two concave edges as previously described, the maximum diameter is located between the opposed convex edges and may be from about 0.25 to about 2.8 mm and more preferably from about 0.3 to about 1.5 mm, although larger and smaller dimensions are certainly within the scope of the present invention. The minimum distance between the opposed concave edges may be from about 0.1 to about 1.5 mm, and preferably from about 0.2 to about 0.9 mm. Other minimum diameters may be used.

By altering the maximum cross-sectional diameter and/or the minimum distance of the pins, the volume of reagent composition deposited with each contact of the substrate may be varied. By altering the ratio of the cross-sectional maximum diameter to the minimum distance of the pins, the spread of the reagent composition and the shape of the resulting deposition may be varied. To provide rectangular depositions, ratios of maximum/minimum cross-sectional dimensions may be from 30 (3/0.1) to 0.17 (0.25/1.5), and preferably from 7.5 (1.5/0.2) to 0.33 (0.3/0.9). Other ratios of maximum/minimum cross-sectional dimensions may be used.

Microdeposition pins may be made from any suitably hard material, such as metal, alloy, silicon, ceramic, plastic, or composite. Preferably, the pins are made from titanium. The shaft and/or the tip of the pin may be treated or coated to alter chemical and/or mechanical properties of the surface. As an example, the tip may be treated with a fluorocarbon to alter hydrophilicity.

In addition to the size and shape of the microdeposition pins, the morphology of the reagent composition also affects the spread and thickness of the resulting deposition. The reagent composition may be in liquid, gel, gellular, colloidal, or other form and may include reagents and optionally a binder. The reagent compositions may have viscosities ranging from about 1 cp to about 100 cp. More preferable reagent compositions have viscosities ranging from about 1 cp to about 20 cp or from about 4 cp to about 10 cp. Reagent compositions with other viscosities may be used.

The constituents present in the reagent composition may include binders, such as polymers; biomolecules, such as enzymes specific to an analyte like glucose oxidase; and electro-active molecules that mediate the flow of electrons between the first and second electrodes, such as the ferrocyanide/ferricyanide redox couple. The reagent compositions may include binders having molecular weights from 10,000 to 900,000, and preferably from 30,000 to 300,000 (weight/average). Binders having other molecular weights may be used. Molecular weights may be determined by size exclusion chromatography (SEC), and are generally expressed as weight averages or number averages.

The binder is preferably a polymeric material that is at least partially water-soluble. The binder may form a gel or gel-like material when hydrated. Suitable partially water-soluble polymeric materials for use as the binder may include poly (ethylene oxide) (PEO), carboxy methyl cellulose (CMC), polyvinyl alcohol (PVA), hydroxyethylene cellulose (HEC), hydroxypropyl cellulose (HPC), methyl cellulose, ethyl cellulose, ethyl hydroxyethyl cellulose, carboxymethyl ethyl cellulose, polyvinyl pyrrolidone (PVP), polyamino acids, such as polylysine, polystyrene sulfonate, gelatin, acrylic acid, methacrylic acid, starch, maleic anhydride salts thereof, derivatives thereof, and combinations thereof. Among the above binder materials, PEO, PVA, CMC, and HEC are preferred, with CMC being more preferred at present for biosensors. Other binders may be used.

The reagent compositions also may include biomolecules having weight/average molecular weights from 10,000 to 500,000 and preferably from 100,000 to 400,000 that maintain biological activity after deposition. Biomolecules may include active enzymes and biopolymers, such as nucleic acids, proteins, and peptides. Other biomolecules may be used. The biomolecules may include amine functional groups capable of hydrogen bonding interactions. Unlike laser ablation and other methods used in the semi-conductor industry to form small features, the present microdeposition pins can form depositions including biomolecules that maintain their biological activity.

Figure 16:
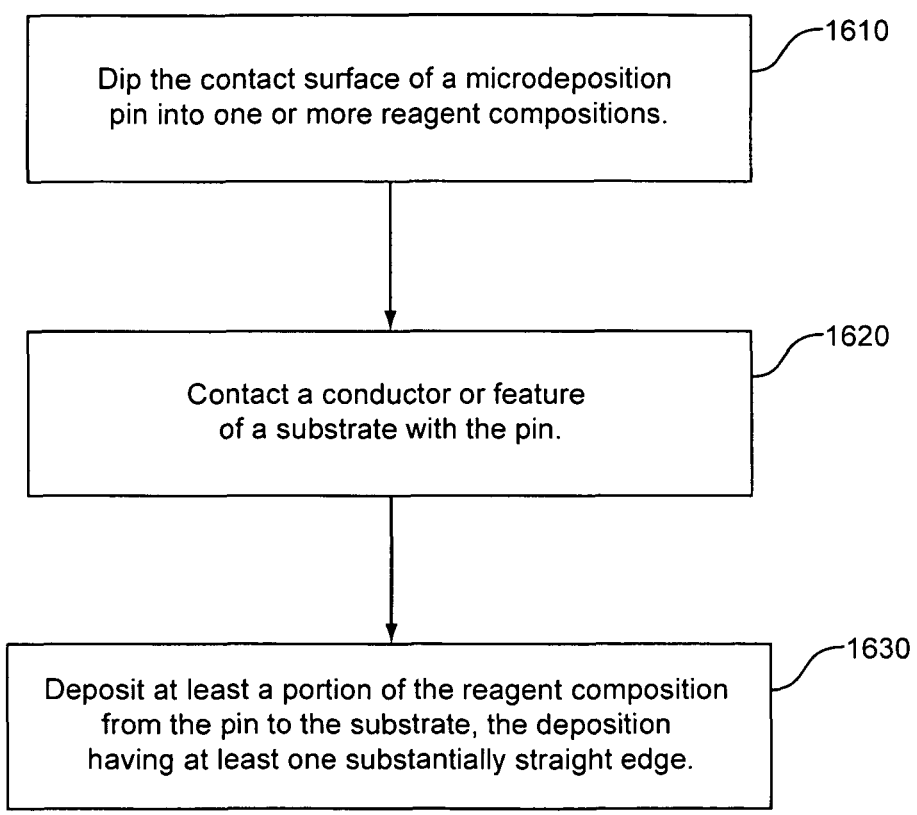
FIG. 16 represents a method of forming a biosensor.

FIG. 16 represents a method 1600 of forming a biosensor. In 1610 the contact surface of a microdeposition pin is dipped into one or more reagent compositions. In 1620, the pin is contacted with a conductor or feature of a substrate. In 1630 at least a portion of the reagent composition from the pin is deposited on the substrate. For an electrochemical biosensor, one or more conductors and or electrodes may be formed on the substrate before, during, or after the deposition. For an optical biosensor, one or more features may be formed on the substrate before, during, or after the deposition. The conductors or other features present on the substrate may be raised, having an average height of from about 5 to about 25 µm above the surface of the substrate. Features having an average height of less than about 5 µm or less than about 1 µm above the surface of the substrate also may be present. The term "average height" of a raised feature or deposition is used because the top surface may be uneven, having peaks and valleys.

To form the sensor strip of an electrochemical biosensor, a first conductor terminating in a first area and a second conductor terminating in a second area may be formed on a planar plastic substrate. The first and second areas may be physically separated or together and may be in flow communication with the sample or a portion of the sample. The terminus of each conductor may have the shape of its respective conductor or a different shape and may be present in a reservoir where the sample is held for analysis. The terminus of each conductor may be formed from the same material as the other portions of the conductor, or from a different material. Preferably, the terminus of each conductor is formed from a non-reactive material, such as carbon, gold, or platinum. As the conductors may establish electrical communication between the sample reservoir and the contacts for connection to the measurement device, they often are rectangular in shape.

Microdeposition pins may be used to apply a first regent composition on the first conductor and a second reagent composition on the second conductor. The reagent composition may be deposited on the termini of the conductors or closer to the contacts. Preferably, at least a portion of the first and second reagent compositions resides within the sample reservoir. The first and second reagent compositions may be the same or may include different reagents to provide the first and second conductors with different electrochemical characteristics. For example, the first reagent composition may be optimized to oxidize or reduce the analyte, while the second reagent composition may be optimized to transfer electrons between the redox reaction of the analyte and the conductor surface.

The closer the spacing between the first and second conductor termini, the less the reagent compositions can spread from the termini and remain separate. Thus, referring back to FIG. 5, for example, substantial overlap of the different reagent compositions was observed. This overlap of the reagent compositions may reduce the benefits of optimizing different reagent compositions for the different conductors. Thus, the smaller the width of the substrate between the conductors, the less reagent composition spreading may occur and maintain the desired separate chemistries at the two conductors.

As the longitudinal length of a conductor may run from the terminus to the contacts, the reagent composition can span any length of the conductor. The reagent composition may span from about 0.5 to about 3 mm of the longitudinal length of the conductor. Preferably, the portion of the conductors where the one or more reagent compositions are deposited has a width of at most 1.5 mm and more preferably of at most 1 mm. The portion of the conductors where the one or more reagent compositions are deposited may have a width of from about 0.2 mm to about 1.2 mm or more preferably from about 0.3 mm to about 1 mm. The portion of the conductors where the one or more reagent compositions are deposited may have other widths. The average thicknesses of the deposited reagent composition may range from about 1 µm to about 2 µm when using from about 0.02 µL to about 5 µL of a reagent composition having a viscosity from about 2 cp to about 10 cp and a maximum pin diameter from about 0.3 mm to about 2.5 mm. Other thicknesses of the deposited reagent may be used.

The reagent composition may spread at most 0.3 mm, at most 0.15 mm, or at most 0.05 mm beyond the conductor. The spread of the reagent composition away from the conductor surface and onto the substrate also may be defined as percent substrate spread by dividing the distance the reagent composition spreads onto the substrate by the width of the conductor. Thus, a reagent composition spread of about 0.1 mm beyond a conductor having an about 1 mm width gives an about 100% substrate spread. The sensor strips may have reagent composition substrate spreads of at most 20%, preferably at most 15%, and more preferably at most 8%. The reagent composition substrate spreads may range from about 1% to about 4% or more preferably from about 1% to about 2% are preferred. The reagent composition may not spread on the substrate, thus providing an essentially 0% substrate spread. Other reagent composition substrate spreads may be used.

Figure 15:
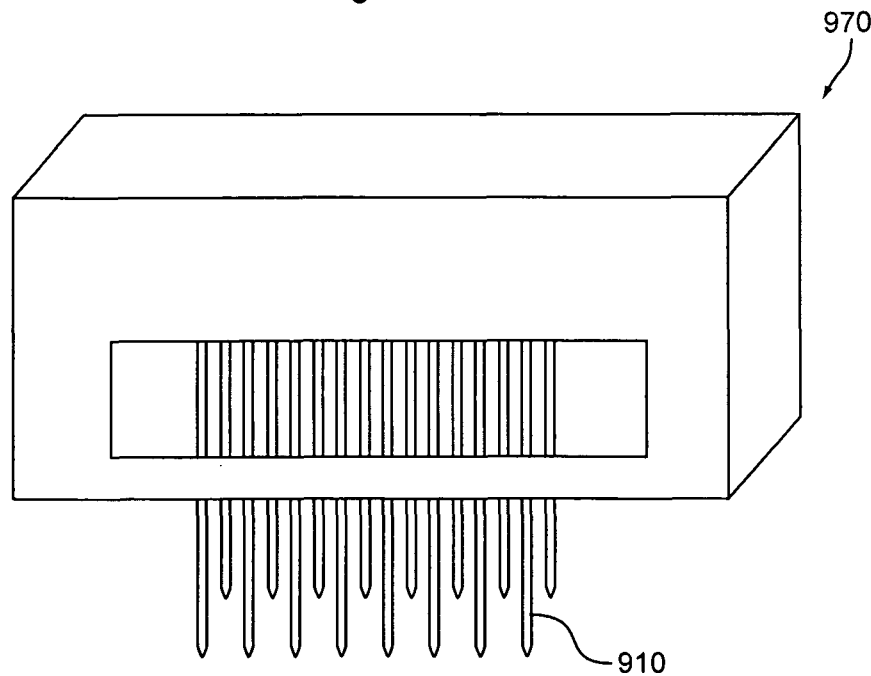
FIG. 15 illustrates a holder including multiple microdeposition pins.

In another aspect of the present invention, a holder 970 may be provided so as to employ multiple pins 910 simultaneously. For example, as shown in FIG. 15, multiple pins 910 may be combined in a holder 970, to provide multiple depositions with one contact of a substrate (not shown in the figure). The holder 970 may be attached to a motion control system (not shown) for automated movement of the microdeposition pins in multiple dimensions. The microdeposition pin 910 may be fitted with mounting collars, such as collar 14 as represented in FIG. 3A, to assist in affixing multiple pins in the holder 970.

While various aspects of the present invention have been described, it will be apparent to those of ordinary skill in the art that other embodiments and implementations are possible within the scope of the invention.

What is claimed is:

1. A microdeposition pin, comprising:
   a shaft terminating in a head, the head having:
      a base,
      a contact surface including at least two convex and at least two concave edges,
      the cross-section of the contact surface having a maximum diameter between two convex edges from about 0.25 mm to about 3 mm, having a minimum distance between two concave edges from about 0.1 mm to about 1.5 mm, and having a ratio of the maximum diameter to the minimum distance of from 7.5 to 0.33, and
      side surfaces connecting the base to the contact surface and including a concave side wall.

2. The pin of claim 1, wherein said contact surface further includes a flat edge.

3. The pin of claim 1, wherein said side surfaces include a first side wall that is approximately perpendicular to said contact surface.

4. The pin of claim 1, wherein said side surfaces include a first side wall that is angled relative to said contact surface of the pin.

5. The pin of claim 1, wherein said side surfaces include a concave side wall intersecting said contact surface to form one of the concave edges, wherein said concave side wall extends substantially the length of said head.

6. The pin of claim 1, wherein said side surfaces include a concave side wall intersecting said contact surface to form one of the concave edges, wherein said concave side wall is tapered along a length of said head.

7. The pin of claim 1, wherein said head includes a channel therein terminating at an aperture disposed at said contact surface.

8. The pin of claim 1, further comprising a collar remote from said head of said pin, said collar adapted for affixing said pin to a holder.

9. The pin of claim 1, the cross-section of the contact surface having the maximum diameter from about 2 mm to about 3 mm, the minimum distance from about 1 mm to about 1.5 mm, and a maximum arc distance from about 1.3 mm to about 1.4 mm, where a radius defines the arc of at least one of the concave edges, and the radius has a length from about 3 mm to about 4 mm.

10. An apparatus for the deposition of a reagent composition, the apparatus comprising:
    at least one microdeposition pin comprising:
       a shaft terminating in a head, the head having:
          a base;
          a contact surface including at least two convex and at least two concave edges, where the cross-section of the contact surface has a maximum diameter between two convex edges from about 0.25 mm to about 3 mm, has a minimum distance between two concave edges from about 0.1 mm to about 1.5 mm, and has a ratio of the maximum diameter to the minimum distance of from 7.5 to 0.33;
          side surfaces connecting the base and the contact surface and including a concave side wall; and
       a holder for grasping said at least one microdeposition pin such that said contact surface is remote from said holder.

11. A method of forming a reagent composition footprint, comprising:
    depositing an amount of the reagent composition onto a contact surface of a pin, said contact surface having at least two convex edges and at least two concave edges, where the cross-section of the contact surface has a maximum diameter between two convex edges from about 0.25 mm to about 3 mm, has a minimum distance between two concave edges from about 0.1 mm to about 1.5 mm, and has a ratio of the maximum diameter to the minimum distance from 7.5 to 0.33; and
    engaging said contact surface of said pin with a substrate to form a reagent composition deposition on the substrate, the reagent composition deposition comprising a footprint having at least one substantially straight edge.

12. The apparatus of claim 10, wherein said at least one microdeposition pin includes a plurality of microdeposition pins, wherein each pin includes a contact surface having at least two convex and at least two concave edges; where the cross-section of the contact surface of each pin has a maximum diameter between two convex edges from about 0.25 mm to about 3 mm, has a minimum distance between two concave edges from about 0.1 mm to about 1.5 mm, and has a ratio of the maximum diameter to the minimum distance of from 7.5 to 0.33.

13. The apparatus of claim 12, where the cross-section of the contact surface of each pin has the maximum diameter from about 2 mm to about 3 mm, the minimum distance from about 1 mm to about 1.5 mm, and a maximum arc distance from about 1.3 mm to about 1.4 mm, where a radius defines the arc of at least one of the concave edges, and the radius has a length from about 3 mm to about 4 mm.

14. The apparatus of claim 10, where the cross-section of the contact surface has the maximum diameter from about 2 mm to about 3 mm, the minimum distance from about 1 mm to about 1.5 mm, and a maximum arc distance from about 1.3 mm to about 1.4 mm, where a radius defines the arc of at least one of the concave edges, and the radius has a length from about 3 mm to about 4 mm.

15. The method of claim 11, where the reagent composition deposition comprises a footprint having at least two substantially straight edges.

16. The method of claim 15, where the reagent composition deposition is rectangular in shape.

17. The method of claim 15, where the deposition has a length of from about 0.15 mm to about 3.2 mm, and a width of from about 0.2 mm to about 1.2 mm.

18. The method of claim 15, where the deposition has a thickness of about 1 μm to about 2 μm.

19. A microdeposition pin, comprising:
    a shaft terminating in a head, the head having:
       a base;
       a contact surface including:
          a first convex edge;
          an opposing second convex edge;
          a first concave edge connecting the first and second convex edges at respective first ends thereof;
          an opposing second concave edge connecting the first and second convex edges at respective second ends thereof; and
          side surfaces connecting the base to the contact surface and including a concave side wall that forms one of the first and second concave edges,
       wherein the cross-section of the contact surface includes:
          a maximum diameter between the first and second convex edges from about 0.25 mm to about 3 mm; and
          a minimum distance between the first and second concave edges from about 0.1 mm to about 1.5 mm.

20. The pin of claim 19, wherein the concave side wall is approximately perpendicular to the contact surface.

21. The pin of claim 19, wherein the concave side wall is tapered along a length of the head.

22. The pin of claim 19, wherein the head includes a channel therein terminating at an aperture disposed at the contact surface.

23. The pin of claim 19, further comprising a collar remote from the head of the pin, the collar adapted for affixing the pin to a holder.

24. The pin of claim 19, the cross-section of the contact surface having the maximum diameter from about 2 mm to about 3 mm, the minimum distance from about 1 mm to about 1.5 mm, and a maximum arc distance from about 1.3 mm to about 1.4 mm, where a radius defines the arc of at least one of the first and second concave edges, and the radius has a length from about 3 mm to about 4 mm.

\* \* \* \* \*

UNITED STATES PATENT AND TRADEMARK OFFICE
CERTIFICATE OF CORRECTION

| | | |
|---|---|---|
| PATENT NO. | : 9,182,393 B2 | Page 1 of 1 |
| APPLICATION NO. | : 12/132954 | |
| DATED | : November 10, 2015 | |
| INVENTOR(S) | : Huan-Ping Wu | |

It is certified that error appears in the above-identified patent and that said Letters Patent is hereby corrected as shown below:

IN THE SPECIFICATION

In Column 10, Lines 4-5, delete "50% to about 100%." and insert -- 5% to about 10%. --, therefor.

In Column 10, Line 42, delete "gel, gellular," and insert -- gel, cellular, --, therefor.

In Column 12, Line 43, delete "about 100%" and insert -- about 10% --, therefor.

Signed and Sealed this
Twenty-third Day of February, 2016

Michelle K. Lee
*Director of the United States Patent and Trademark Office*